United States Patent
Weng et al.

(10) Patent No.: US 9,226,950 B2
(45) Date of Patent: Jan. 5, 2016

(54) METHOD AND COMPOSITION FOR TREATING DIABETES MELLITUS

(71) Applicant: National Dong Hwa University, Hualien (TW)

(72) Inventors: Ching-Feng Weng, Hualien (TW); Chin-piao Chen, Hualien (TW); Yi-Chen Chia, Hualien (TW); Chia-Yu Hsu, Hualien (TW)

(73) Assignee: National Dong Hwa University, Hualien (TW)

( * ) Notice: Subject to any disclaimer, the term of this patent is extended or adjusted under 35 U.S.C. 154(b) by 0 days.

(21) Appl. No.: 14/077,310

(22) Filed: Nov. 12, 2013

(65) Prior Publication Data

US 2015/0133371 A1     May 14, 2015

(51) Int. Cl.
*A61K 38/00* (2006.01)
*C07K 9/00* (2006.01)
*A61K 38/28* (2006.01)
*A61K 31/045* (2006.01)

(52) U.S. Cl.
CPC ............... *A61K 38/28* (2013.01); *A61K 31/045* (2013.01)

(58) Field of Classification Search
CPC ...... A61K 45/06; A61K 9/1617; A61K 31/00
See application file for complete search history.

(56) References Cited

U.S. PATENT DOCUMENTS

2006/0165671 A1* 7/2006 Raederstorff et al. ....... 424/94.1
2009/0258896 A1* 10/2009 Jain et al. ...................... 514/299

FOREIGN PATENT DOCUMENTS

WO    WO 2012027159 A1 * 3/2012

* cited by examiner

*Primary Examiner* — Christina Bradley
*Assistant Examiner* — Jeanette Lieb
(74) *Attorney, Agent, or Firm* — Fox Rothschild LLP

(57) ABSTRACT

The present invention relates to a method or composition for glycemic control in a subject, which is effective for treating diabetes mellitus, comprising administering the subject with a pharmaceutical composition comprising a therapeutically effective amount of an aliphatic alcohol having a general formula of $CH_3(CH_2)_nCH_2OH$, wherein n is an integer from 10 to 40, such as tetracosanol, and a pharmaceutically acceptable carrier.

16 Claims, 6 Drawing Sheets

METHOD AND COMPOSITION FOR TREATING DIABETES MELLITUS

FIELD OF THE INVENTION

The present invention relates to a method and composition for treating diabetes mellitus.

BACKGROUND OF THE INVENTION

Type 2 diabetes mellitus (T2DM) is the most common chronic diseases and high prevalence in worldwide. A global estimate in the prevalence of diabetes indicates a growing burden, particularly in developing countries. The major symptom of type 2 diabetes is high levels of glucose in the blood. The recent long-term mega trials showed that intensive glycemic control could reduce the aggravation of insulin resistance and T2DM symptom (Avogaro, "Treating diabetes today with gliclazide MR: a matter of numbers." *Diabetes Obes Metab* 14 Suppl 1: 14-19, 2012). This is the reason why insulin-sensitizing agents become more valuable for the glycemic control. However, it is still desirable to develop a method and pharmaceutical composition with low toxicity, preferably from natural compounds for treatment of diabetes mellitus, particular in T2DM.

Levin provided a composition consisting essentially of a refined oil carrier, and a non-toxic physiologically active compound selected from the class consisting of octacosanol, triacontanol, tetracosanol, and hexacosanol; and a method of increasing oxygen utilization in human beings comprising administering to human being a pharmaceutical composition comprising the composition (U.S. Pat. No. 3,031,376, 1962).

Clark provided a treatment for inflammatory skin diseases through a topical application of an ointment base containing triaconstanol (U.S. Pat. No. 4,670,471, 1987).

Granja et al. provides a mixture of higher primary aliphatic alcohols of 22 to 38 carbon atoms that can be obtained by saponifying and extracting steps with organic solvents from sugar cane wax. It was disclosed that the mixture contains tetracosanol, hexacosanol, heptacosanol, octacosanol, nonacosanol, triacotanol, dotriacontanol, and tetratriacontanol, and it can be used for the treatment of hypercholesterolemia and atherosclerotic complications as platelet hyperaggregabiulity, ischemia, and thrombosis, the prevention of drug induced gastric ulcer and the improvement of male sexual activity (U.S. Pat. No. 5,663,156, 1997).

Recently, Fuenzalida Diaz et al. provided a process to obtain tetracosanol from a complex mixture derived from tall oil pitch (US Patent Publication No. 2012/0125762 al, 2012).

BRIEF SUMMARY OF THE INVENTION

It is unexpected found in the invention that an aliphatic alcohol of $CH_3(CH_2)_nCH_2OH$ is effective in the glycemic control, in which can be used for treatment of diabetes mellitus, particularly type 2 diabetes mellitus (T2DM).

In one aspect, the invention provides a method for glycemic control in a subject comprising administering the subject with a pharmaceutical composition comprising a therapeutically effective amount of an aliphatic alcohol having a general formula of $CH_3(CH_2)_nCH_2OH$, wherein n is an integer from 10 to 40, and a pharmaceutically acceptable carrier.

In the other aspect, the invention provides a method for treating diabetes mellitus with the aliphatic alcohol, particularly type 2 diabetes mellitus (T2DM).

In a further aspect, the invention provides a method for treating diabetes mellitus with insulin or an insulin analogous in combination of the aliphatic alcohol.

In a yet aspect, the invention provides a pharmaceutical composition for treating diabetes mellitus comprising insulin or an insulin analogue in combination of the aliphatic alcohol at the ratio effective in sensitization or synergy of insulin function by targeting IRK through the mechanism by GLUT4 translocation and insulin signaling pathway.

In the embodiment of the invention, herein n is 18, 20, 22, 24, 26, 28 or 30.

In the embodiments of the invention, the aliphatic alcohol is selected from the group consisting of octadecanol, docosanol, tetracosanol, triacontanol, and combination thereof.

In one example of the invention, the aliphatic alcohol is tetracosanol.

In one embodiment of the invention, the diabetes mellitus is type 2 diabetes mellitus.

In a particular embodiment of the invention, the subject is a patient suffered from diabetes mellitus with insulin resistance.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 5(a) shows the blood glucose change (compared the value at the 0 min) of each group of mice treated without (Con)/with S961 (DM), and then treated with Metformin (Met) as a positive control or with tetracosanol (Tet), and administered with D-glucose (2 g/kg Bwt); in which the data were expressed as means±SE, and different letters represent the significant differences (p<0.05) among various treatments.

FIG. 5(b) shows the AUC (area under curve) of the blood glucose change of each group of mice treated without (Con)/with S961 (DM), and then treated with Metformin (Met) as a positive control or with tetracosanol (Tet), and administered with D-glucose (2 g/kg Bwt); in which the data are expressed as means with standard errors of mean, and different letters represent the significant differences (p<0.05) among various treatments.

FIG. 6(a) shows the blood glucose change (compared the value at the 0 min.) of each group of mice treated without (Con)/with S961 (DM), and then treated with Metformin (Met) as a positive control, or with octadecanol ($CH_3(CH_2)_{16}CH_2OH$, containing 18 carbon atoms, represented by $C_{18}OH$), docosanol ($CH_3(CH_2)_{20}CH_2OH$, containing 22 carbon atoms, represented by $C_{22}OH$), tetracosanol ($CH_3(CH_2)_{22}CH_2OH$, containing 24 carbon atoms, represented by $C_{24}OH$), or triacontanol ($CH_3(CH_2)_{28}CH_2OH$, containing 30 carbon atoms, represented by $C_{30}OH$), and administered with D-glucose (2 g/kg Bwt); in which the data were expressed as means±SE, and different letters represent the significant differences (p<0.05) among various treatments.

FIG. 6(b) shows the AUC (area under curve) of the blood glucose change of each group of mice treated without (Con)/with S961 (DM), and then treated with Metformin (Met) as a positive control, or with octadecanol ($C_{18}OH$), docosanol ($C_{22}OH$), tetracosanol ($C_{24}OH$), or triacontanol ($C_{30}OH$), and administered with D-glucose (2 g/kg Bwt); in which the data were expressed as means±SE, and different letters represent the significant differences (p<0.05) among various treatments.

FIG. 7(a) shows the blood glucose change (compared the value at the 0 min) of each group of mice treated without (Con)/with S961 (DM), and then treated with Metformin (Met) as a positive control, or with the tetracosanol ($CH_3(CH_2)_{22}CH_2OH$, containing 24 carbon atoms, represented by $C_{24}OH$) with a modification of a hydroxyl group by a sulfonic acid (represented by $C_{24}SO_3H$), by a thiol (represented by $C_{24}SH$), by an amine (represented by $C_{24}NH_2$), and administered with D-glucose (2 g/kg Bwt) (n=6 in each group); in which the data were expressed as means±SE, and different letters represent the significant differences (p<0.05).

FIG. 7(b) shows the AUC (area under curve) of the blood glucose change (compared the value of the mice at the 0 min) of each group of mice treated without (Con)/with S961 (DM), and then treated with Metformin (Met) as a positive control, or with the tetracosanol with a modification of a hydroxyl group by a sulfonic acid ($C_{24}SO_3H$), by a thiol ($C_{24}SH$), by an amine ($C_{24}NH2$), and administered with D-glucose (2 g/kg Bwt) (n=6 in each group); in which the data were expressed as means±SE, and different letters represent the significant differences (p<0.05).

DETAILED DESCRIPTION OF THE INVENTION

Figure 1A:
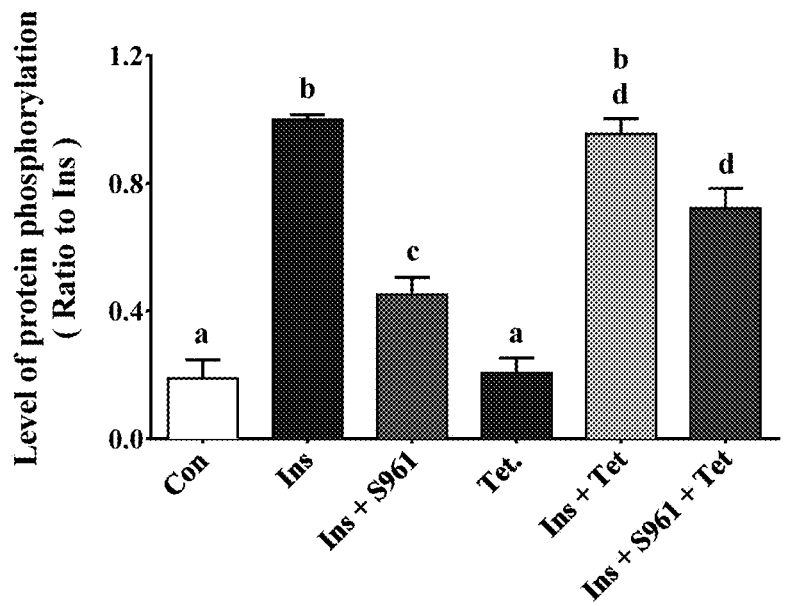
FIG. 1(a) shows the effect of tetracosanol on the phosphorylation of Insr protein; wherein the L6 cell lysates of the controls and treated groups were separated by SDS-PAGE and blotted for phospho-Insr on Tyr1158, 1162, and 1163 (Insr, 100 kDa), and the protein level was measured by Western blot analysis; in which the data were expressed as means with standard errors of mean (mean±SEM), and different letters represent the significant differences ($p<0.05$) among various treatments.

Unless otherwise defined, all technical and scientific terms used herein have the same meaning as commonly understood by one of ordinary skill in the art to which this invention pertains. In the case of conflict, the present document, including definitions will be controlled.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "subject" refers to a human or a mammal, such as a patient, a companion animal (e.g., dog, cat, and the like), a farm animal (e.g., cow, sheep, pig, horse, and the like) or a laboratory animal (e.g., rat, mouse, rabbit, and the like).

It is known that insulin stimulates intracellular signaling pathways that regulate insulin receptor (Insr) extracellular α-chains resulted in auto-phosphorylation of specific tyrosine residues at Tyr1158, Tyr1162, and Tyr1163 sites of the activating loop (A-loop) in the insulin receptor kinase (IRK) domain located the cytoplasmic portion of the β-chains, is critical for the stimulation of kinase activity (Rosen et al., "Phosphorylation activates the insulin receptor tyrosine protein kinase." Proceedings of the National Academy of Sciences of the United States of America 80(11): 3237-3240, 1983; and Ellis et al., "Replacement of insulin receptor tyrosine residues 1162 and 1163 compromises insulin-stimulated kinase activity and uptake of 2-deoxyglucose." Cell 45(5): 721-732, 1986). Lack of insulin-stimulation, the unphosphorylated Tyr1162 residues of A-loop competes with ATP and protein substrates for binding at the kinase active site. The binding of insulin to the Insr, insulin-triggered auto-phosphorylation of the tyrosine residues within the A-loop, conformational change of IRK segment which enhances the kinase activity. When insulin triggers glucose uptake in muscle and adipose tissue through the stimulation of glucose transporter 4 (GLUT4) vesicles translocated from intracellular sites to the plasma membrane. Following the phosphorylating tyrosine of Insr, the PI3-K/Akt (PKB) pathway is critical to glucose transport in several tissues including muscle, especially through GLUT4 translocation (Son et al., "Cardiomyocyte expression of PPARγ leads to cardiac dysfunction in mice." J. Clin. Invest. 117(10): 2791-2801, 2007; and Shisheva, "Phosphoinositides in insulin action on GLUT4 dynamics: not just PtdIns (3,4,5)P3." American journal of physiology. Endocrinology and metabolism 295(3): E536-544, 2008). Thus GLUT4 is a major mediator for glucose uptake from the circulation and a key regulator of whole-body glucose homeostasis (Huang and Czech, "The GLUT4 glucose transporter." *Cell metabolism* 5(4): 237-252, 2007).

According to the invention, it is evidenced in the examples that tetracosanol or aliphatic alcohols containing different carbon numbers are effective in the enhancement of GLUT4 translocation, in the improvement of glucose uptake, and possess potential for glycemic control in the hyperglycemic mice (DM mice), particularly those with insulin resistance.

Accordingly, the invention provides a method for glycemic control in a subject comprising administering the subject with a pharmaceutical composition comprising a therapeutically effective amount of an aliphatic alcohol having a general formula of $CH_3(CH_2)_nCH_2OH$, wherein n is an integer from 10 to 40, and a pharmaceutically acceptable carrier.

Further, the invention provides a method for treating diabetes mellitus in a subject. The method comprises administering the subject with a pharmaceutical composition comprising a therapeutically effective amount of an aliphatic alcohol having a general formula of $CH_3(CH_2)_nCH_2OH$, wherein n is an integer from 10 to 40, and a pharmaceutically acceptable carrier.

In addition, the invention provides a new use of an aliphatic alcohol having a general formula of $CH_3(CH_2)_nCH_2OH$, wherein n is an integer from 10 to 40, for manufacturing a pharmaceutical composition for treating diabetes mellitus.

The invention also provides a pharmaceutical composition for treating diabetes mellitus comprising a therapeutically effective amount of the aliphatic alcohol.

In addition, it is confirmed in the present invention that tetracosanol is effective in sensitization or synergy of insulin function by targeting IRK through the mechanism by GLUT4 translocation and insulin signaling pathway. Thus, the method of the invention may comprise administering the subject with the aliphatic alcohol in combination of insulin or an insulin analogue, wherein the aliphatic alcohol is at the amount sufficient to be effective in sensitization or synergy of insulin function.

Furthermore, the invention provides a pharmaceutical composition for treating diabetes mellitus comprising insulin or an insulin analogue in combination of the aliphatic alcohol as defined in claim 1 at the ratio effective in sensitization or synergy of insulin function by targeting IRK through the mechanism by GLUT4 translocation and insulin signaling pathway.

In the present invention, the examples of the aliphatic alcohol of $CH_3(CH_2)_nCH_2OH$ include the aliphatic alcohols containing more than 10 carbon atoms and less than 40 carbon atoms. For example, the aliphatic alcohol may contain 18, 20, 22, 24, 26, 28, and 30 carbon atoms respectively. Preferred examples include octadecanol, docosanol, tetracosanol, and triacontanol. A more preferred example is tetracosanol, containing 22 carbon atoms. It is believed that any combination of the aliphatic alcohols provides the same effect in treatment of diabetes mellitus.

The term "tetracosanol" as used herein refers to a compound of $CH_3(CH_2)_{22}CH_2OH$, which has a chemical structure below:

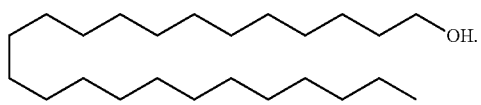 [SMILES: CCCCCCCCCCCCCCCCCCCCCCCCO]

The term "therapeutically effective amount" as used herein refers to an amount of an agent sufficient to achieve the intended purpose. For example, an effective amount of tetracosanol to treat diabetes mellitus is an amount sufficient for glycemic control or for treatment of diabetes mellitus in a subject. The therapeutically effective amount of a given agent will vary with factors such as the nature of the agent, the route of administration, the size and species of the animal to receive the agent, and the purpose of the administration. The therapeutically effective amount in each individual case may be determined empirically by a skilled artisan according to the disclosure herein and established methods in the art.

The term "insulin analogous" as used herein, also called as "insulin receptor ligand," refers to an altered form of insulin, different from any occurring in nature, but still available to the human body for performing the same action as human insulin in terms of glycemic control. Insulin analogous may be obtained through genetic engineering of the underlying DNA, the amino acid sequence of insulin with modification to alter its absorption, distribution, metabolism, and excretion characteristics. The examples of insulin analogous include but are not limited to those illustrated in Hirsch, "Insulin analogues", New England J Med 2005; 352:174-183, 2005.

The pharmaceutical composition of the invention may be administered in any route that is appropriate, including but not limited to parenteral or oral administration. The pharmaceutical compositions for parenteral administration include solutions, suspensions, emulsions, and solid injectable compositions that are dissolved or suspended in a solvent immediately before use. The injections may be prepared by dissolving, suspending or emulsifying one or more of the active ingredients in a diluent. Examples of said diluents are distilled water for injection, physiological saline, vegetable oil, alcohol, and a combination thereof. Further, the injections may contain stabilizers, solubilizers, suspending agents, emulsifiers, soothing agents, buffers, preservatives, etc. The injections are sterilized in the final formulation step or prepared by sterile procedure.

According to the invention, the composition may be administered through oral route, wherein the composition may be in a solid or liquid form. The solid compositions include tablets, pills, capsules, dispersible powders, granules, and the like. The oral compositions also include gargles which are to be stuck to oral cavity and sublingual tablets. The capsules include hard capsules and soft capsules. In such solid compositions for oral use, one or more of the active compound(s) may be admixed solely or with diluents, binders, disintegrators, lubricants, stabilizers, solubilizers, and then formulated into a preparation in a conventional manner. When necessary, such preparations may be coated with a coating agent, or they may be coated with two or more coating layers. On the other hand, the liquid compositions for oral administration include pharmaceutically acceptable aqueous solutions, suspensions, emulsions, syrups, elixirs, and the like. In such compositions, one or more of the active compound(s) may be dissolved, suspended or emulsified in a commonly used diluent (such as purified water, ethanol or a mixture thereof, etc.). Besides such diluents, said compositions may also contain wetting agents, suspending agents, emulsifiers, sweetening agents, flavoring agents, perfumes, preservatives and buffers and the like.

The specific example below is to be construed as merely illustrative, and not limitative of the remainder of the disclosure in any way whatsoever. Without further elaboration, it is believed that one skilled in the art can, based on the description herein, utilize the present invention to its fullest extent.

EXAMPLES

Materials

The higher primary aliphatic alcohols of tetracosanol was provided by Dr. Yi-Chen Chia (Department of Food Technology, Tajen University, Pingtung, Taiwan) and extracted from sugar cane.

The aliphatic alcohols containing 18, 22, 24, and 30 carbon atoms respectively (including octadecanol, docosanol, tetracosanol, and triacontanol), and the tetracosanols with modification of the hydroxyl group by a sulfonic acid ($SO_3H$), a thiol (SH), an amine ($NH_2$) respectively were obtained from Dr. Chin-Paio Chen at Department of Chemistry, National Dong-Hwa University (Hualien, Taiwan).

S961 (insulin receptor antagonist) were a generous gift from Dr. Lauge Schäffer (Novo-Nordisk, Denmark).

Insulin was purchased from Novo-Nordisk, (DK-4400, Kalundborg, Denmark).

Statistical Analysis

All of the data in these examples were expressed as means±SEM. The Statistical analysis was performed using GraphPad Prism software. Statistical comparisons of the results were made using one-way analysis of variance (ANOVA). The means of the groups in one test were compared each other, and different letters represent significant differences at $p<0.05$ by Tukey's test.

Example 1

Effect of Tetracosanol on Phosphorylation of Insr and AKT 1.1 Cell Culture and Maintenance of Mouse Muscle Myoblast Cells (L6)

Mouse muscle myoblast cells (L6) was a generous gift from Professor Hitoshi Ashida's Lab. (Kobe University, Kobe, Japan). The cells were grown and maintained in α-minimal essential medium (α-MEM, 12000022, GIBCO, CA, USA) containing 10% fetal bovine serum (FBS, GIBCO) and 1% penicillin streptomycin (GIBCO) in a cell culture incubator with 5% $CO_2$ at 37° C. Prior to the following experiments, the cells were seeded and cultured at a density of $8\times10^3$ cells per well in 96-well plates or $2.5\times10^5$ cells per well in 6-well plates. After the myoblasts achieved 80% confluence, the cells were incubated for 5 days in the α-MEM supplemented with 2% FBS to induce differentiation to myotubes.

1.2 Phosphorylation of Insulin Receptors (Tyr1158/Tyr1162/Tyr1163)

L6 cells were fully differentiated with α-MEM supplemented with 2% FBS for 5 days to myotubes. The cells were washed twice with Phosphate Buffered Saline (PBS) containing 0.1% BSA and subsequently incubated α-MEM containing 0.25% BSA with or without 100 nM of S961, and treated with or without 100 μM of Tetracosanol for 90 min. Then, the cells were treated with or without 10 μM of insulin for 5 min. Finally, the cells were collected and washed twice in KRH buffer (containing 50 mM HEPES, 137 mM NaCl, 4.8 mM KCl, 1.85 mM $CaCl_2$, and 1.3 mM $MgSO_4$), then lysed in ice-cold RIPA buffer (containing 50 mM Tris-HCl, pH 8.0, 150 mM NaCl, 5 mM NaF, 1% NP40, 1 mM sodium orthovanadate, 0.5% sodium deoxycholate, 0.1% sodium dodecyl sulphate (SDS), protease inhibitors and phosphatase inhibitors (DE-68305, Roche, Mannheim, Germany)) for 60 min. After centrifugation at 12,000×g for 30 min at 4° C., the supernatant was kept at −80° C. until use. The levels of the proteins including phospho-Insulin receptors (Tyr1158/Tyr1162/Tyr1163) and Insulin receptor (Cell Signaling, Boston, Mass., USA) were detected and evaluated by Western blot with primary antibody.

1.3 Phosphorylation of AKT on Thr 308 and AMPK on Thr 172

The L6 cells were fully differentiated with α-MEM supplemented with 2% FBS for 5 days to myotubes. The cells were washed twice with PBS containing 0.1% BSA and subsequently incubated α-MEM containing 0.25% BSA with or without 100 nM of S961, and then treated with or without 100 μM of Tetracosanol for 90 min. Then, the cells were treated with or without 10 μM of insulin for 30 min. Finally, the cells were collected and washed twice in KRH buffer, then lysed in ice-cold RIPA buffer for 60 min. After centrifugation at 12,000×g for 30 min. at 4° C., the supernatant was kept at −80° C. until use. The levels of the proteins including phospho-AKT (Thr308), AKT, phospho-AMPK (Thr172), and AMPK (Cell Signaling) were detected and evaluated by Western blot with primary antibody.

1.4 Western Blot

The cells after treatments were collected and washed twice in cold KRH buffer, and then lysed in ice-cold RIPA buffer incubation at 4° C. for 60 min. After centrifugation at 12,000×g for 30 min at 4° C., the supernatant was kept and quantified by Bradford protein assay (Bio-Rad, Hercules, Calif., USA). The proteins were separated using sodium dodecyl sulfate polyacrylamide gel electrophoresis (SDS-PAGE) and subsequently transferred to PVDF (Perkin Elmer Life Sciences, Boston, Mass., USA) membrane. The blots were blocked with 5% non-fat milk in TBS/T (20 mM Tris-Base, 137 mM NaCl at pH 7.4 and 0.05% Tween-20) at RT for 1 hr and then incubated with the appropriate primary antibody at 4° C. overnight. After wash, the blots were incubated with horseradish peroxidise (HRP)-conjugated secondary antibody (General Electric, Little Chalfont, Buckinghamshire, UK) for additional 1 hr. The signals were monitored using Western Lightning™ Plus-ECL (Perkin Elmer Life Sciences) and the PVDF membrane was exposed to Luminescent image analyzer (LAS)-3000 (Fujifilm, Minato, Tokyo, Japan). Acquired data were analyzed and compared the difference among treatments.

1.5 Effect of Tetracosanol in Increasing the phosphorylation of Insr and AKT

The differentiated L6 cells were incubated with 100 μM of tetracosanol (Tet) at 37° C. for 90 min, and then treated 10 μM of insulin (Ins) at 37° C. for 5 or 30 min. The cell lysates were separated by SDS-PAGE and blotted 5 min for phospho-Insr on Tyr1158, 1162, and 1163 (Insr, 100 kDa), and phospho-AKT on Thr308 protein level was measured at 30 min in Western blot analysis.

Figure 1B:
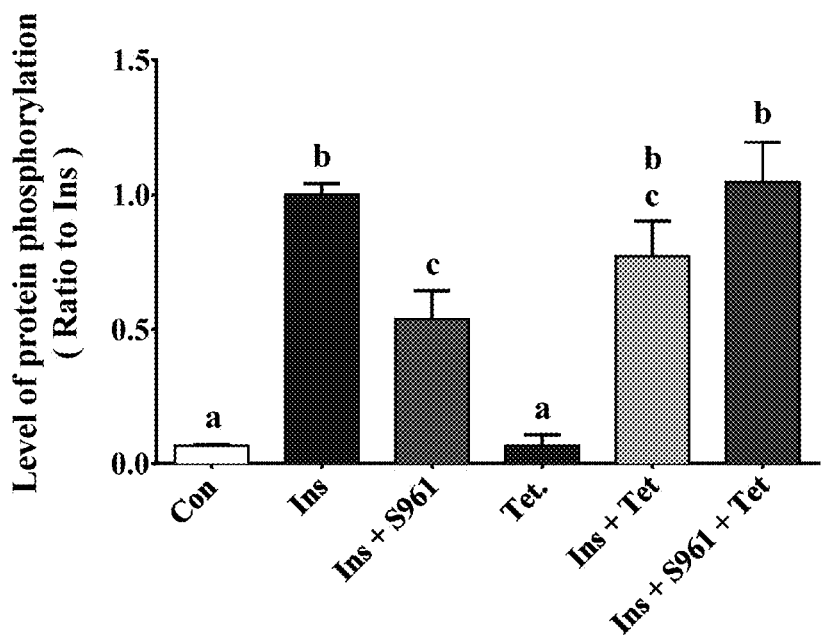
FIG. 1(b) shows the effects of tetracosanol on the phosphorylation of AKT proteins; wherein the L6 cell lysates were separated by SDS-PAGE and blotted for phospho-AKT on Thr308, and the protein level was measured by Western blot analysis; in which the data were expressed as means with standard errors of mean (mean±SEM), and different letters represent the significant differences ($p<0.05$) among various treatments.

It is known that GLUT4 translocation requires insulin-dependent PI3K/AKT activation signaling pathway in skeletal muscle, and the activation of Insr and AKT could be a direct evidence to influence of tetracosanol from insulin-dependent pathway. Actually, insulin has been clinically used to control glucose uptake by activating insulin signaling. The results of the phosphorylation of phospho-Insr on Tyr1158, 1162, and 1163 in the mouse myoblast L6 cells treated without (con)/with insulin (Ins), insulin plus S961 (Ins+S961), tetracosanol (Tet), insulin plus tetracosanol (Ins+Tet), insulin plus S961 and tetracosanol (Ins+S961+Tet) were shown in FIG. 1(a), indicating that the phosphorylation activity was tended to be enhanced by insulin (Ins), insulin plus S961 (Ins+S961), insulin plus tetracosanol (Ins+Tet), or insulin with S961 plus tetracosanol (Ins+S961+Tet). The results of further down stream AKT phosphorylation were shown in FIG. 1(b), indicating that insulin (Ins), plus S961 (Ins+S961)

or tetracosanol (Ins+Tet) or both S961 and tetracosanol (Ins+S961+Tet) induced the phospho-AKT on Thr 308, but tetracosanol (Tet) did not.

1.6 Effect of Tetracosanol on Insulin-Independent GLUT4 Translocation Response

Figure 2:
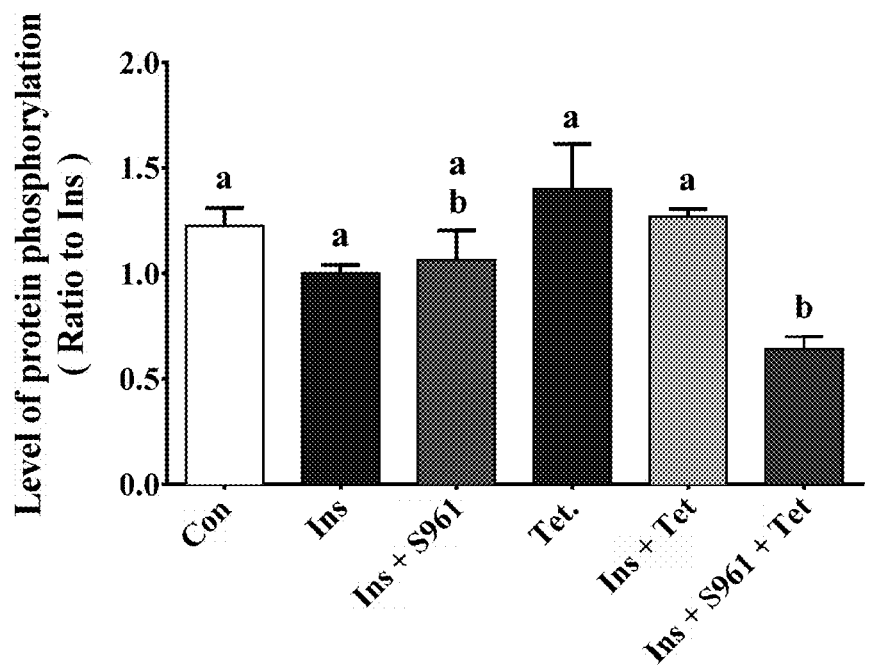
FIG. 2 shows the effect of tetracosanol on the phosphorylation of AMPK protein; wherein the L6 cell lysates of the controls and the treated groups were separated by SDS-PAGE and blotted for the phospho-AMPK on Thr172, and the protein level were measured by Western blot analysis; in which the data were expressed as means±SE, and different letter represents the significant difference ($p<0.05$) among various treatments.

The differentiated L6 cells were incubated with 100 µM tetracosanol (Tet) at 37° C. for 90 min, and then treated with 10 µM of insulin (Ins) at 37° C. for additional 30 min. The cell lysates were separated by SDS-PAGE and blotted for phospho-AMPK on Thr172, and the protein level was measured by Western blot analysis. It is known that the GLUT4 translocation requires insulin-dependent PI3K/AKT activation signaling pathway or insulin-independent AMPK activation pathway in skeletal muscle. As shown in FIG. 2, tetracosanol possessed no insulin-independent GLUT4 translocation response.

Example 2

2.1 Cell Culture and Maintenance of Mouse Muscle Myoblast Cells (C2C12)

Mouse muscle myoblast cells (C2C12) were obtained from the Food Industry Research and Development Institute (FIRDI, Hsinchu, Taiwan). The cells were grown and maintained in Dulbecco's Modified Eagle's Medium high glucose (DMEM-high glucose; GIBCO, CA, USA) containing 10% fetal bovine serum (FBS, GIBCO) and 1% penicillin streptomycin (GIBCO) in a cell culture incubator with 5% $CO_2$ at 37° C. Prior to the following experiments, the cells were seeded and cultured at a density of $8\times10^3$ cells per well in 96-well plates or $2.5\times10^5$ cells per well in 6-well plates. After the myoblasts achieved 80% confluence, the cells were incubated for 4 days in the high glucose DMEM supplemented with 1% FBS and 1% horse serum to induce differentiation to myotubes.

2.2 Measurement of GLUT4 Translocation

The C2C12 cells were fully differentiated with DMEM supplemented with 1% FBS and 1% horse serum for 4 days. The cells were washed twice with PBS containing 0.1% BSA and subsequently incubated PBS with or without 20 nM S961 for 15 min., then treated with or without 100 µM of tetracosanol, and administered with or without 185 µM of insulin for 40 min. The translocation changes of GLUT4 of the cells were detected. The cells were placed on ice and immediately fixed with 1% glutaraldehyde in PBS at room temperature (RT) for 10 min. After quenching with 0.1 M glycine in PBS for 10 min., the cells were blocked with PBS containing 5% mouse serum for 30 min. To determine the cell surface GLUT4 content, the cells were incubated for 1 hr. with anti-GLUT4 antibody (Santa Cruz, Calif., USA) that was diluted to 1 µg/ml in PBS containing 3% mouse serum. Then, the cells were treated with a secondary antibody-horseradish peroxidase (HRP)-conjugated anti-Goat IgG (Jackson ImmunoResearch, Suffolk, UK) diluted 1:300 in PBS containing 3% mouse serum for 1 hr. After a rinsing step with PBS, 3,3',5,5'-Tetramethylbenzidine (TMB) substrate (BioLegend, CA, USA) was added and reacted at RT for 30 min., and then 2N $H_2SO_4$ was added to stop the reaction. The HRP activity was determined by measuring the absorbance at 450 nm with a spectrophotometer (EnSpire 2300 Multilabel Reader, Perkin Elmer, Waltham, Mass., USA).

2.3 Synergistic Effect of Tetracosanol plus Insulin on Glut4 translocation

Figure 3:
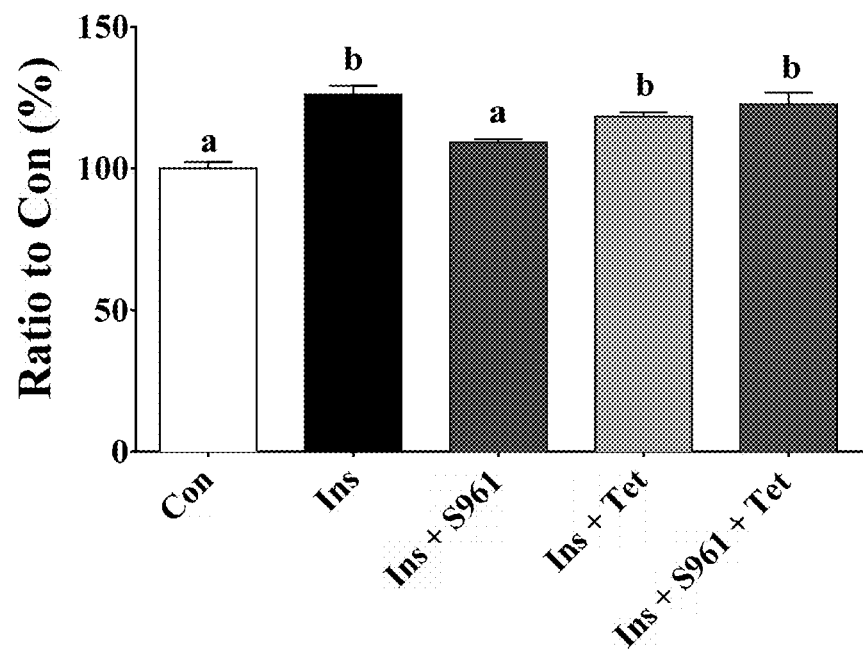
FIG. 3 shows the regulatory effect of four potential compounds on GLUT4 translocation; wherein the C2C12 cells were treated with 20 nM of S961 (S961) followed by 185 µM of insulin (Ins) and 100 µM of Tetracosanol (Tet) (n=4 in each group); in which the data were expressed as means±SE, and different letter represents the significant difference (p<0.05) among various treatments.

To detect the effect of tetracosanol on Glut4 translocation in S961-induced insulin resistance, the differentiated C2C12 cells were treated with or without 20 nM S961 (S961) followed by 185 µM of insulin (Ins), and treated with or without 100 µM of Tetracosanol (Tet) (n=4 in each group). The glucose uptake was through recruitment of GLUT4 to the plasma membrane (GLUT4 translocation) where these transporters facilitate glucose uptake. At the cellular level, the ability of glucose uptake was determined by controlling the amount of the GLUT4 glucose transporter present in the plasma membrane. The ability of tetracosanol to enhance GLUT4 translocation was evaluated by GLUT4 translocation assay. As shown in FIG. 3, tetracosanol provided no effects on the insulin-dependent GLUT4 translocation in the normal C2C12 differentiated myotubes (Ins); however in the insulin resistance C2C12 differentiated myotubes induced by S961 (Ins+S961), the treatment with insulin plus tetracosanol (Ins+Tet), or insulin with tetracosanol plus S961 (Ins+Tet+S961) provided the recovery ability to the insulin-dependent GLUT4 translocation in vitro.

2.4 Glucose Uptake Assay

The glucose uptake assay was followed the study disclosed in Yamamoto et al. ("An enzymatic fluorimetric assay to quantitate 2-deoxyglucose and 2-deoxyglucose-6-phosphate for in vitro and in vivo use." *Anal Biochem* 404(2): 238-240, 2010) with minor modification and the technique generously assistant from Professor Hitoshi Ashida's Lab (Kobe University, Kobe, Japan). The differentiated L6 myotubes seeding in 96 well microplates were incubated with 100 µl/well of α-MEM containing 2% FBS and pre-treated with 10 µM tetracosanol overnight. Then, the medium was changed by 0.25% BSA in the presence 1 µM insulin, 400 nM S961, and 10 µM tetracosanol and incubated for 30 min. After incubation, the cells were washed twice with KRH buffer. The L6 myotubes were then incubated with KRH buffer containing 1 mM of 2-deoxyglucose (2DG, Sigma-Aldrich, St. Louis, Mo., USA) and 60 µl of 0.1% BSA in 5% $CO_2$ at 37° C. for 20 min. After incubation, the cells were washed twice with KRH buffer and then 50 µl of 0.1N NaOH per well was added. The microplates were dried by incubation at 85° C. for 90 min. The components in the wells were then neutralized by the addition of 50 µl of 0.1 N HCl and then 50 µl of 50 mM triethanolamine hydrochloride (TEA) buffer (200 mM KCl, 200 mM TEA pH 8.1) was added. Uptake of 2DG into the cells was measured by the enzymatic fluorescence assay. The fluorescence assay buffer was composed of 50 mM TEA buffer, 0.1% BSA, 2.5 mM β-NADP (Wako Pure Chemical, Osaka, Japan), 0.05 unit Diaphorase (Wako), 150 unit/L. mesenteriodes G6PDH (sigma), and 0.5 mM Resazurin sodium salt (sigma). 10 µl of 2DG sample with 100 µl of fluorescence assay buffer were reacted at 37° C. for 30 min. At the end of the incubation, fluorescence at 570 nm with excitation at 540 nm was measured by spectrophotometer (EnSpire 2300 Multilabel Reader, Perkin Elmer, Waltham, Mass., USA).

2.5 Tetracosanol Enhanced the Glucose Uptake

The differentiated L6 myotubes were seeded in 96 well microplate and incubated with 100 µl/well of α-MEM containing 2% FBS, and then pre-treated with 10 µM tetracosanol overnight. The medium was changed by 0.25% BSA in the presence 1 µM insulin, with and without 400 nM S961, and then treated with and without 10 µM tetracosanol for 30 min (n=4 in each group).

Figure 4:
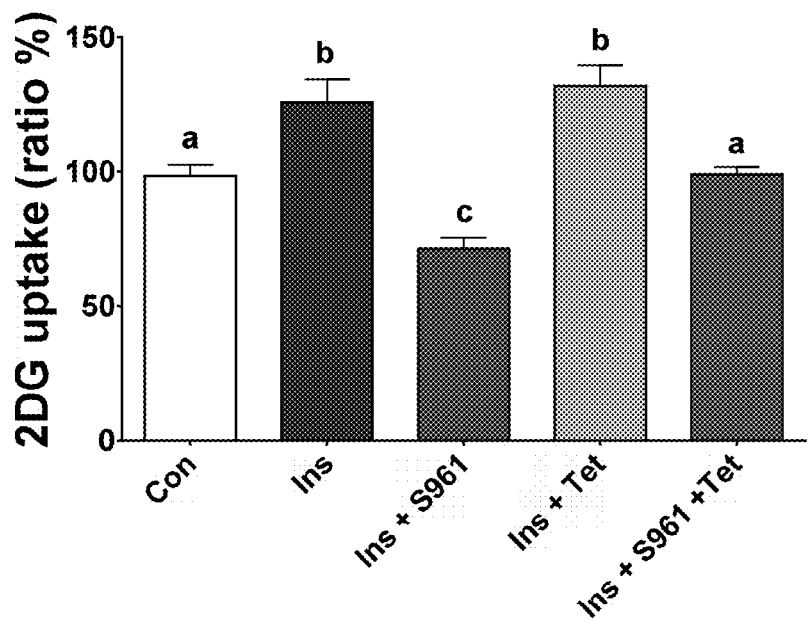
FIG. 4 provides the effect of tetracosanol on the glucose uptake; wherein the L6 myotubes seeded in a 96 well microplate were incubated with 100 µl/well of α-MEM containing 2% FBS, and pre-treated with 10 µM tetracosanol overnight; and then the medium in each well was changed by 0.25% BSA in the presence 1 µM insulin (Ins), 400 nM S961 (S961), and 10 µM tetracosanol (Tet) (n=4 in each group); in which the data were expressed as means±SE, and different letter represents the significant difference (p<0.05) among various treatments.

As shown in FIG. 4, tetracosanol with insulin enhanced the cell glucose uptake; however the treatment with insulin plus both S961 and tetracosanol (Ins+S961+Tet) provided a synergistic effect over that of the treatment with tetracosanol plus insulin (Ins+Tet).

Example 3

Animal Test of Tetracosanol

3.1 Animals

Animal experiments were approved by the National Dong-Hwa University Animal Ethics Committee and were used according to the "Guide for the Care and Use of Laboratory Animals" of National Dong-Hwa University. The C57BL/6 mouse were obtained National Laboratory Animal Center (Taipei, Taiwan) and kept at controlled environmental conditions with room temperature (22±2° C.) and humidity (50±10%). The 12 hr light (0600 am-1800 pm) and 12 hr dark cycle was maintained throughout the study. Mice had free access to food and water and maintained on a standard laboratory diet (containing carbohydrates: 60%, proteins: 28%, lipids: 12%, and vitamins: 3%).

3.2 Efficacy of Tetracosanol on Short Term Glucose Tolerance in Insulin Resistance Mice The 8 weeks old male C57 BL/6 mice after fasting 12 hr were used in this test. The mice were orally administered (p.o.) with tetracosanol (dissolved in PEG and EtOH, 25 mg/kg Bwt) or Metformin (100 mg/kg Bwt) for 3 hr. To investigate the effect of tetracosanol on the DM mice, the mice were intraperitoneally injected (i.p.) with S961 (50 nmol/kg Bwt) to induce hyperglycemia, prior to the administration of D-glucose (2 g/kg Bwt, p.o.). At approximately the 0, 30, 60, 90, and 120 min., the blood of each mouse was sampled by venipuncture from the tail vein for the determination of blood glucose. Blood glucose was immediately determined by the glucose oxidase method using glucose analyzer (Accu-Chek, Roche).

Figure 5A:
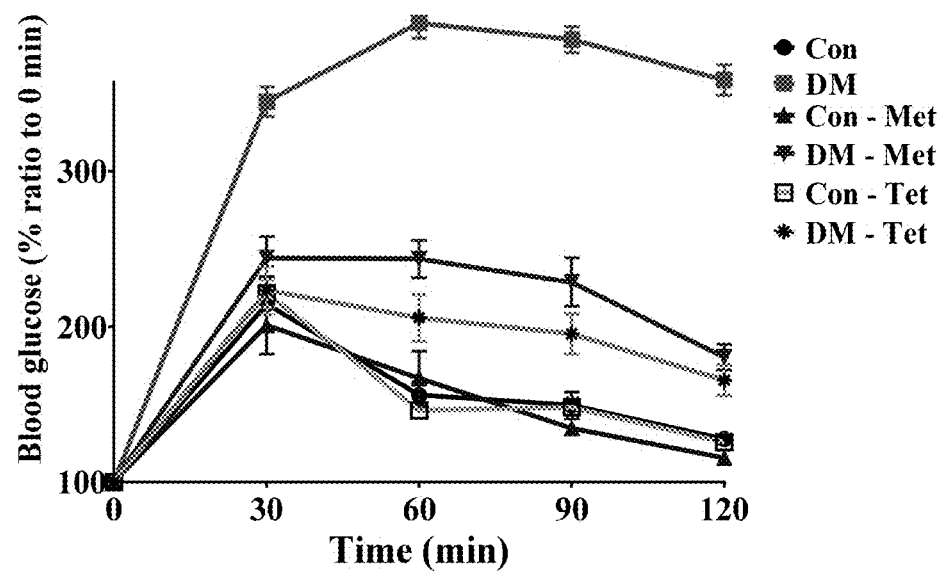
FIGS. 5(a) and 5(b) show the hypoglycemic efficacy of tetracosanol in oral glucose tolerance test (OGTT) in controls (without a treatment with S961, Con) and mimic diabetes mellitus mice (DM)
Figure 5B:
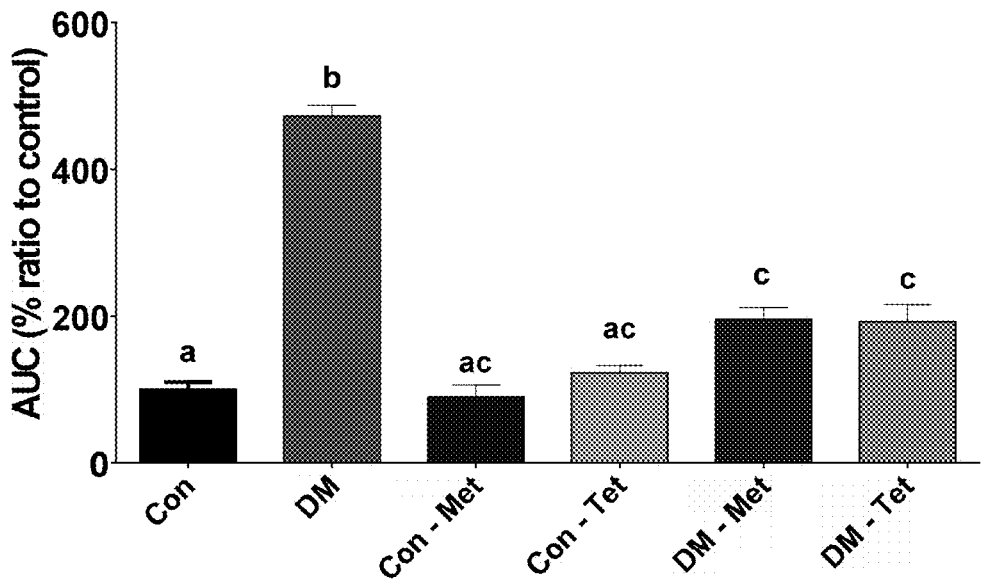

3.3 Tetracosanol Ameliorated Blood Glucose of S961-Induced Hyperglycemic Mice in OGTT To investigate the glycemic control effect of tetracosanol on the hyperglycemic mice, hyperglycemic mice were induced by insulin receptor antagonist-S961. The mice of each group were treated with or without Metformin (Met) as positive control, or treated with or without tetracosanol (Tet). Then, all the groups were administered with D-glucose (2 g/kg Bwt) (n=6 in each group). The tetracosanol for glycemic control was confirmed by OGTT. As shown in FIG. 5(a), the treatment with tetracosanol provided a profile similar to the treatment with metformin but only quarter dose of tetracosanol was needed. FIG. 5(b) showed that tetracosanol had good efficacy in glycemic control in DM mice (DM), like normal mice (Con). It was suggested that tetracosanol serve as a potential agent for glycemic control via enhancement of glucose transporter 4 translocation that improves glucose uptake.

Example 4

Effect of Tetracosanols Modified by Carbon Numbers and Hydroxyl Group

4.1 Efficacy of Tetracosanols with Different Carbon Numbers

To study what functional group of a tetracosanol structure provides effect in glycemic control of the hyperglycemic mice, the hyperglycemic mice were treated with various tetracosanols with modification on the carbon number and the hydroxyl group.

Figure 6A:
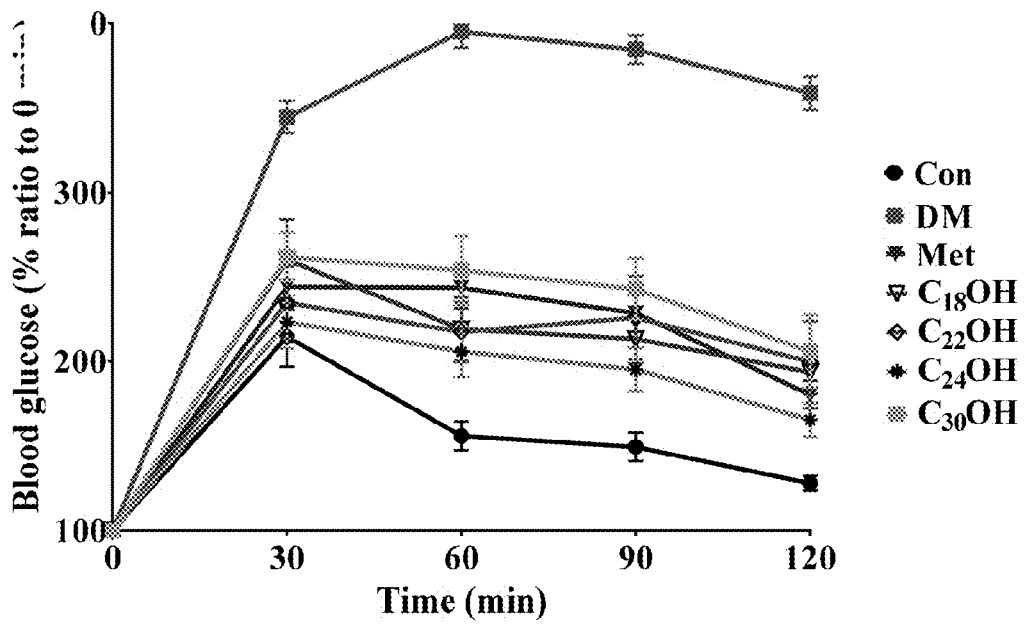
FIGS. 6(a) and 6(b) show the hypoglycemic efficacy of tetracosanols with different carbon numbers on oral glucose tolerance test (OGTT)
Figure 6B:
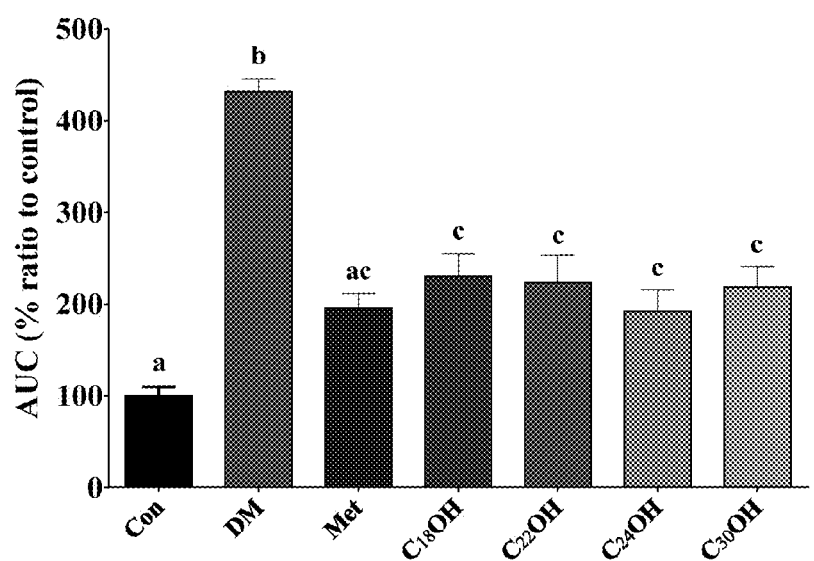

8 weeks old male C57 BL/6 mice after fasting 12 hr were employed in this study. The mice were intraperitoneally injected (i.p.) with S961 (an insulin receptor antagonist, 50 nmol/kg Bwt) to induce hyperglycemia so as to produce hyperglycemic mice (DM mice). The DM mice were orally administered (p.o.) with Metformin (Met) as positive control, or with the aliphatic alcohols containing 18, 22, 24, and 30 carbon atoms respectively, i.e., octadecanol ($C_{18}OH$), docosanol ($C_{22}OH$), tetracosanol ($C_{24}OH$), triacontanol ($C_{30}OH$). There were 6 mice in each group. After an administration of D-glucose (2 g/kg Bwt), the blood of each mouse was sampled by venipuncture from the tail vein for the determination of blood glucose at approximately the 0, 30, 60, 90, and 120 min. The blood glucose was determined by the glucose oxidase method using glucose analyzer (Accu-Chek, Roche). The blood glucose change (compared to the value at the 0 min.) of each group was shown in FIG. 6(a), and the AUC (area under curve) of each group was shown in FIG. 6(b). It was indicated in FIG. 6(a) and FIG. 6(b) that the aliphatic alcohols with different lengths or carbon numbers provided similar glycemic control effects. No matter whether the length of an aliphatic alcohol is extended or shortened, the aliphatic alcohol showed good efficacy similar to tetracosanol and had profile similar to that of metformin (see Figures and 6(a) and 6(b)). Tetracosanol ($C_{24}OH$) was even better than metformin (see in FIG. 6(a)).

4.2 Efficacy of Tetracosanols with Modifications on Hydroxyl Group

Figure 7A:
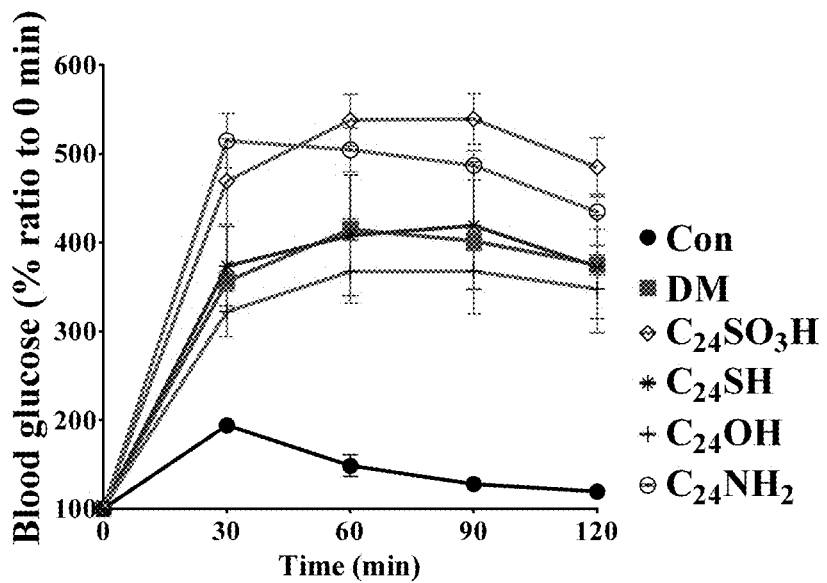
FIGS. 7(a) and 7(b) show the hypoglycemic efficacy of modified tetracosanols on oral glucose tolerance test (OGTT)
Figure 7B:
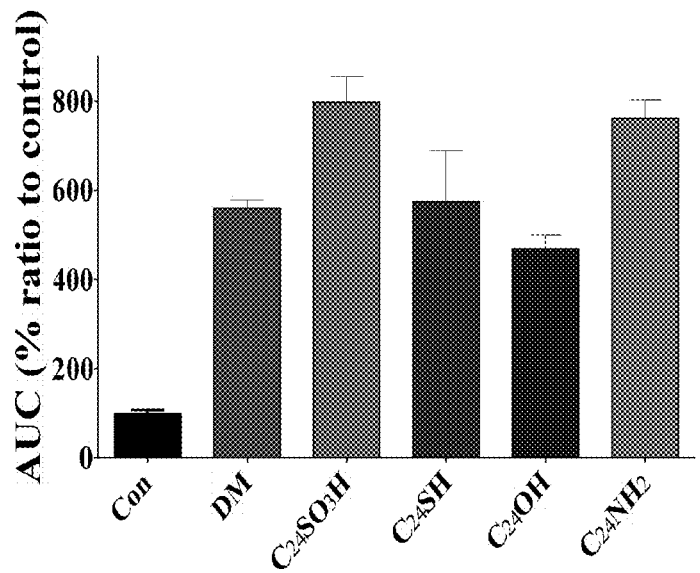

The same study of glycemic control effect on the DM mice was performed to investigate the effect of the hydroxyl group of the tetracosanol structure. The tetracosanols were chemically modified on the hydroxyl group by a sulfonic acid ($SO_3H$—), thiol (SH—), or amine (NH2-) group, and then were dissolved in PEG and EtoH for administration. The DM mice were treated with Metformin (100 mg/kg Bwt) as positive control or the modified tetracosanols (25 mg/kg Bwt). The blood glucose change (compared to the value at the 0 min), and AUC (area under curve) of the mice of each group were determined. As shown in FIGS. 7(a) and 7(b), the tetracosanol with the group other than hydroxyl group had no glycemic control effect on the hyperglycemic mice, and the hydroxyl group tended to get good efficacy for glycemic control. It was suggested in this study that tetracosanol may serve as a potential agent for glycemic control via hydroxyl group.

In view of the results of the in vitro and in vivo studies provided above, it is concluded that tetracosanol or aliphatic alcohols containing different carbon numbers possess potential for glycemic control via the enhancement of glucose transporter 4 translocation improved glucose uptake, and thus it can be developed as a drug for treating diabetes mellitus, particularly type 2 diabetes mellitus.

We claim:

1. A method for glycemic control in a subject comprising administering to the subject a pharmaceutical composition comprising a single aliphatic alcohol as the sole active ingredient, wherein the aliphatic alcohol has a general formula of $CH_3(CH_2)_nCH_2OH$ and contains in total 18-30 carbon atoms, in an amount effective in glycemic control in said subject, where n is an integer, and a pharmaceutically acceptable carrier.

2. The method of claim 1, wherein the aliphatic alcohol is selected from the group consisting of octadecanol ($C_{18}OH$), docosanol ($C_{22}OH$), tetracosanol ($C_{24}OH$) and triacontanol ($C_{30}OH$).

3. The method of claim 1, wherein the aliphatic alcohol is tetracosanol.

4. The method of claim 1, which is effective for glycemic control in diabetes mellitus.

5. The method of claim 4, wherein the diabetes mellitus is type 2 diabetes mellitus.

6. The method of claim 1, wherein the subject is a patient suffering from diabetes mellitus with insulin resistance.

7. The method of claim 1, wherein the aliphatic alcohol improves glucose uptake.

8. The method of claim 1, wherein the aliphatic alcohol provides an effect on a sensitization or synergy of insulin function.

9. A method for glycemic control in diabetes mellitus in a subject comprising administering to the subject a pharmaceutical composition comprising a single aliphatic alcohol as the sole active ingredient, wherein the aliphatic alcohol has a general formula of $CH_3(CH_2)_nCH_2OH$ and contains in total 18-30 carbon atoms, in an amount effective in glycemic control in said subject, wherein n is an integer, and a pharmaceutically acceptable carrier.

10. The method of claim 9, wherein the aliphatic alcohol is selected from the group consisting of octadecanol ($C_{18}OH$), docosanol ($C_{22}OH$), tetracosanol ($C_{24}OH$) and triacontanol ($C_{30}OH$).

11. The method of claim 9, wherein the aliphatic alcohol is tetracosanol.

12. The method of claim 9, wherein the diabetes mellitus is type 2 diabetes mellitus.

13. The method of claim 9, wherein the subject is a patient suffering from diabetes mellitus with insulin resistance.

14. The method of claim 9, wherein the amount effective is in an amount effective in sensitization or synergy of insulin function.

15. The method of claim 1, wherein the amount effective in glycemic Control in a subject of an aliphatic alcohol is 25 mg/kg body weight.

16. The method of claim 9, wherein the amount effective in glycemic control of an aliphatic alcohol is 25 mg/kg body weight.

* * * * *